United States Patent
Moriguchi et al.

(10) Patent No.: US 10,899,729 B2
(45) Date of Patent: Jan. 26, 2021

(54) METHOD FOR PRODUCING BICYCLIC COMPOUND

(71) Applicant: ONO PHARMACEUTICAL CO., LTD., Osaka (JP)

(72) Inventors: Hideki Moriguchi, Osaka (JP); Yusuke Tanaka, Osaka (JP); Tatsunori Ino, Osaka (JP); Tohru Kambe, Osaka (JP); Taihei Nishiyama, Osaka (JP); Shinichiro Tsujiyama, Osaka (JP); Yohei Ueda, Osaka (JP)

(73) Assignee: ONO PHARMACEUTICAL CO.. LTD., Osaka (JP)

( * ) Notice: Subject to any disclaimer, the term of this patent is extended or adjusted under 35 U.S.C. 154(b) by 0 days.

(21) Appl. No.: 16/314,555

(22) PCT Filed: Jun. 29, 2017

(86) PCT No.: PCT/JP2017/024031
§ 371 (c)(1),
(2) Date: Dec. 31, 2018

(87) PCT Pub. No.: WO2018/003945
PCT Pub. Date: Jan. 4, 2018

(65) Prior Publication Data
US 2019/0315705 A1 Oct. 17, 2019

(30) Foreign Application Priority Data

Jun. 30, 2016 (JP) .................................. 2016-129877

(51) Int. Cl.
*C07D 313/06* (2006.01)
*C07C 69/65* (2006.01)
*C07C 69/75* (2006.01)
*C07D 307/937* (2006.01)

(52) U.S. Cl.
CPC ............ *C07D 313/06* (2013.01); *C07C 69/65* (2013.01); *C07C 69/75* (2013.01); *C07D 307/937* (2013.01)

(58) Field of Classification Search
CPC .............. C07D 313/06; C07D 307/937; C07D 307/935; C07C 69/75; C07C 69/65; C07C 69/76
USPC ...................................................... 549/355
See application file for complete search history.

(56) References Cited

U.S. PATENT DOCUMENTS

| | | | |
|---|---|---|---|
| 4,230,721 A | 10/1980 | Gandolfi et al. | |
| 4,367,237 A | 1/1983 | Wakatsuka et al. | |
| 4,490,537 A | 12/1984 | Johnson | |
| 6,583,174 B1 | 6/2003 | Ueno et al. | |
| 8,614,340 B2 | 12/2013 | Kambe et al. | |
| 8,962,868 B2 | 2/2015 | Kambe et al. | |
| 9,029,574 B2 | 5/2015 | Kambe et al. | |
| 9,388,157 B2 | 7/2016 | Kambe et al. | |
| 9,889,114 B2 | 2/2018 | Kambe et al. | |
| 10,201,520 B2 | 2/2019 | Kambe et al. | |
| 2006/0035949 A1 | 2/2006 | Donde et al. | |
| 2012/0122964 A1 | 5/2012 | Kambe et al. | |
| 2013/0217879 A1 | 8/2013 | Zheng | |
| 2013/0324577 A1 | 12/2013 | Kambe et al. | |

FOREIGN PATENT DOCUMENTS

| | | |
|---|---|---|
| JP | 50-37780 A | 4/1975 |
| JP | 53-84959 A | 7/1978 |
| JP | 53-132573 A | 11/1978 |
| JP | 55-73678 A | 6/1980 |
| JP | 64-68367 A | 3/1989 |
| JP | 2013-532174 A | 8/2013 |
| WO | 01/27099 A2 | 4/2001 |
| WO | 2007/149829 A2 | 12/2007 |
| WO | 2011/013651 A1 | 2/2011 |
| WO | 2012/102355 A1 | 8/2012 |
| WO | 2012/102357 A1 | 8/2012 |

OTHER PUBLICATIONS

Extended European Search Report dated Dec. 3, 2012, issued by the European patent application in counterpart No. 10804397.7.
International Search Report (PCT/ISA/210) dated Mar. 13, 2012, issued by the International Searching Authority in counterpart International Patent Application No. PCT/JP2012/051721.
International Search Report (PCT/ISA/210) dated Mar. 13, 2012, issued by the International Searching Authority in related International Patent Application No. PCT/JP2012/051718.
International Search Report (PCT/ISA/210) dated Sep. 14, 2010, issued by the International Searching Authority in related International Patent Application No. PCT/JP2010/062587.
Anthony R. West, "Solid State Chemistry and Its Applications", Chapter 10 Solid Solutions, John Wiley & Sons, 1984, 3 pages.
Manfred E. Wolff, "Burger's Medicinal Chemistry and Drug Discovery", vol. 1: Principles and Practice, Fifth Edition, John Wiley & Sons, New York, 1997, 4 pages.
Shinsaku Yamane et al., "IOP-Lowering Effect of ONO-9054, A Novel Dual Agonist of Prostanoid EP3 and FP Receptors, in Monkeys", Investigative Ophthalmology & Visual Science, vol. 56, No. 4, The Association for Research in Vision and Ophthalmology, Inc., 2015, pp. 2547-2552.
International Search Report (PCT/ISA/210) dated Oct. 3, 2017, issued by the International Searching Authority in International Application No. PCT/JP2017/024031.
A. L. Hurski et al., "Synthesis of Epothilone with the Forced Application of Oxycyclopropane Intermediates", Russian Journal of Organic Chemistry, vol. 47, No. 11, Pleiades Publishing, Jul. 18, 2011, pp. 1653-1674.

(Continued)

*Primary Examiner* — Taylor V Oh
(74) *Attorney, Agent, or Firm* — Sughrue Mion, PLLC

(57) ABSTRACT

A method for producing a compound, such as 2-propanyl 4-{(3S,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}butanoate, and a novel intermediate suitable for the method, whereby the compound can be stably supplied with a high total reaction yield, by changing the starting material and improving the metathesis reaction, asymmetric reduction reaction and the like.

5 Claims, No Drawings

(56) References Cited

OTHER PUBLICATIONS

Isamu Sugimoto et al., "Discovery of Novel Seven-Membered Prostacyclin Analogues as Potent and Selective Prostaglandin FP and EP3 Dual Agonists", ACS Medicinal Chemistry Letters, vol. 8, No. 1, American Chemical Society, 2017, pp. 107-112.
Marriott et al., Pharmaceutical Compound and Dispensing, Second Edition, 2010, pp. 1-288.
Ansel et al.,, Pharmaceutical Dosage Forms and Drug Delivery Systems, Lippincott Williams & Wilkins, pp. 48-53, 1999.

METHOD FOR PRODUCING BICYCLIC COMPOUND

TECHNICAL FIELD

The present invention relates to a method for producing a bicyclic compound represented by the following general formula (K), which is useful as an intermediate for the manufacture of a medicine or as a drug substance for a medicine. Among others, the present invention relates to a method for producing 2-propanyl 4-{(3S,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}butanoate (hereinafter sometimes abbreviated as the present compound), which can provide the same even on an industrial production scale in a good reaction yield.

BACKGROUND ART

The bicyclic compound which can be produced by the present invention has an FP agonist activity and is known as a medicine useful as a prophylactic and/or therapeutic agent for ocular diseases and the like (see Patent Literature 1). Among others, 2-propanyl 4-{(3 S,5aR,6R,7R,8aS)-6-[(1E, 3R)-4-(2,5-difluorophenoxy)-3-hydroxy-1-buten-1-yl]-7-hydroxyoctahydro-2H-cyclopenta[b]oxepin-3-yl}butanoate is known as Sepetaprost (International Nonproprietary Name) and the development as a therapeutic agent for glaucoma is underway.

Various production methods have been examined in providing the present compound as a drug substance for a medicine. For example, a method for producing the present compound (hereinafter sometimes abbreviated as a known production method) described in Example 16 (25) described in Patent Literature 1 is known. However, the known production method has the following three problems. That is, it has turned out that there have been problems such as: (1) the total number of steps is as large as 16 steps; (2) the yield by a metathesis reaction is low; and (3) the yield of a desired diastereomer is low in an asymmetric reduction reaction. Due to such problems in the known production method, it has been considered that the total reaction yield is low and the synthesis cost becomes high in manufacturing the present compound on an industrial production scale. Therefore, there has been a demand for a method for producing the present compound which solves the problems of the known production method, which is suitable for an industrial production scale, which has a high total reaction yield and which can stably supply the present compound.

CITATIONS LIST

Patent Literature

Patent Literature 1: WO 2011/013651 A

SUMMARY OF INVENTION

Technical Problems

An object of the present invention is to provide a method for producing a compound represented by the general formula (K), particularly a method for producing the present compound, which solves various problems of the known production method and is suitable for an industrial production scale, and a novel intermediate suitable for the production method.

Solutions to Problems

As a result of intensive studies to solve the above-described problems, the present inventors have found a method for producing a compound represented by the general formula (K) which surprisingly solves these problems by changing the starting material, and improving the metathesis reaction, asymmetric reduction reaction, and the like, and have completed the present invention.

That is, the present invention relates to:
[1] A method for producing a compound represented by the general formula (K):

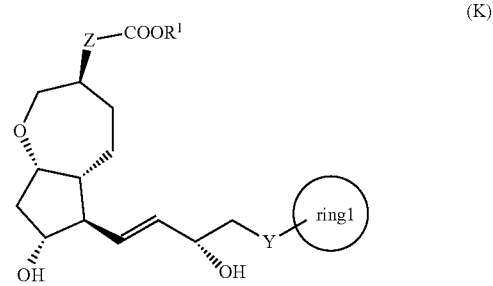

wherein, Y represents —$CH_2$—, —O— or —S—, ring 1 represents a C3-10 carbocycle or a 3- to 10-membered heterocycle optionally substituted with 1 to 5 substituents selected from the group consisting of (1) a halogen atom, (2) $CF_3$, (3) $OCF_3$, (4) a C1-4 alkoxy group, (5) a C1-4 alkyl group, (6) a hydroxyl group, and (7) a nitrile group, $R^1$ represents a C1-6 alkyl group optionally substituted with a hydroxyl group or a C1-4 alkoxy group, Z represents (1) —$(CH_2)_m$—, (2) —$(CH_2)_n$—CH=CH—, or (3) —$(CH_2)_p$-A-$CH_2$—, A represents an oxygen atom, or a sulfur atom, m represents an integer of 1 to 6, n represents an integer of 1 to 4, and p represents an integer of 1 to 4, the method comprising:
step (x): subjecting a compound represented by the general formula (J):

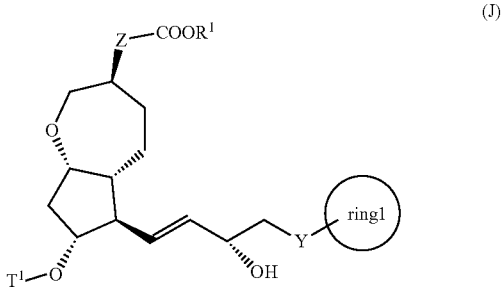

wherein, $T^1$ represents (1) a p-phenybenzoyl group, (2) a methyl group, (3) a trityl group, (4) a methoxymethyl group, (5) a 1-ethoxyethyl group, (6) a methoxyethoxymethyl group, (7) a benzyloxymethyl group, (8) a trimethylsilyl group, (9) a triethylsilyl group, (10) a t-butyldimethylsilyl group, (11) a t-butyldiphenylsilyl group, (12) a triisopropylsilyl group, (13) a benzyl group, (14) a p-methoxybenzyl group, (15) an acetyl group, (16) a pivaloyl group, (17) a benzoyl group, (18) an allyloxycarbonyl group, (19) a 2,2,2-trichloroethoxycarbonyl group, (20) a t-butoxycarbonyl group, (21) an allyl group, or (22) a tosyl group, and other symbols represent the same meanings as those described above, or a salt thereof to a deprotection reaction to produce the compound represented by the general formula (K);

[2] A method for producing the compound represented by the general formula (K) described in the above [1]:

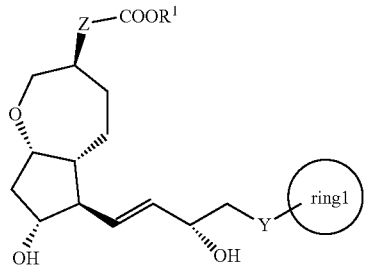

(K)

wherein, all symbols represent the same meanings as those described above,
the method comprising the following steps (ix) to (x):
step (ix): subjecting a compound represented by the general formula (I):

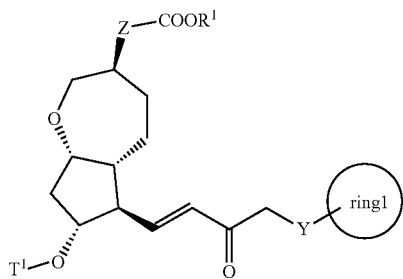

(I)

wherein, all symbols represent the same meanings as those described above, or a salt thereof to an asymmetric reduction reaction to produce the compound represented by the general formula (J) described in the above [1] or a salt thereof; and step (x): subjecting the compound represented by the general formula (J) described in the above [1] or a salt thereof to a deprotection reaction to produce the compound represented by the general formula (K);

[3] A method for producing the compound represented by the general formula (I) described in the above [2] or a salt thereof, the method comprising the following steps (vii) to (viii):

step (vii): subjecting a compound represented by the general formula (G):

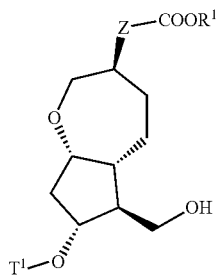

(G)

wherein, all symbols represent the same meanings as those described above, or a salt thereof to an oxidation reaction to produce a compound represented by the general formula (H):

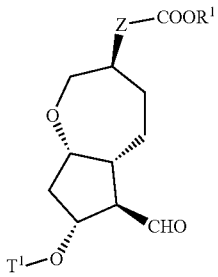

(H)

wherein, all symbols represent the same meanings as those described above; and step (viii): subjecting the compound represented by the general formula (H) obtained in the step (vii) and a compound represented by the general formula (b):

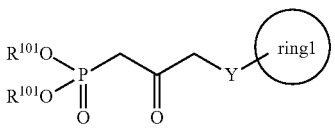

(b)

wherein, $R^{101}$ represents a C1-6 alkyl group, and other symbols represent the same meanings as those described above,
to a reaction in an organic solvent, in water, or in a mixed solution thereof, in the presence of a base, in the presence or absence of an additive to produce the compound represented by the general formula (I) described in the above [2] or a salt thereof;

[4] A method for producing the compound represented by the general formula (G) described in the above [3] or a salt thereof, the method comprising the following steps (i) to (vi):

step (i): subjecting a compound represented by the general formula (A):

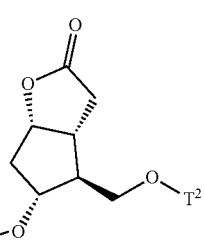

(A)

wherein, $T^2$ represents (1) a p-phenybenzoyl group, (2) a methyl group, (3) a trityl group, (4) a methoxymethyl group, (5) a 1-ethoxyethyl group, (6) a methoxyethoxymethyl group, (7) a benzyloxymethyl group, (8) a trimethylsilyl group, (9) a triethylsilyl group, (10) a tetrahydropyranyl group, (11) a t-butyldiphenylsilyl group, (12) a triisopropylsilyl group, (13) a benzyl group, (14) a p-methoxybenzyl group, (15) an acetyl group, (16) a pivaloyl group, (17) a benzoyl group, (18) an allyloxycarbonyl group, (19) a 2,2,2-trichloroethoxycarbonyl group, (20) a t-butoxycarbonyl group, (21) an allyl group, or (22) a tosyl group, and other symbols represent the same meanings as those described above, to a reduction reaction to produce a compound represented by the general formula (B):

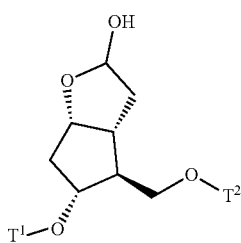

(B)

wherein, all symbols represent the same meanings as those described above, or a salt thereof;

step (ii): subjecting the compound represented by the general formula (B) obtained in the step (i) or a salt thereof to a reaction in an organic solvent, in the presence of a base with using a Wittig reagent to produce a compound represented by the general formula (C):

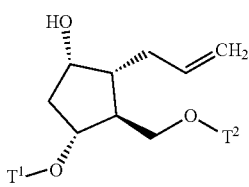

(C)

wherein, all symbols represent the same meanings as those described above, or a salt thereof;

step (iii): subjecting the compound represented by the general formula (C) obtained in the step (ii) or a salt thereof and a compound represented by the general formula (a):

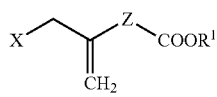

(a)

wherein, X represents a halogen atom, a tosyloxy (TsO) group, or a mesyloxy (MsO) group, and other symbols represent the same meanings as those described above, to an alkylation reaction to produce a compound represented by the general formula (D):

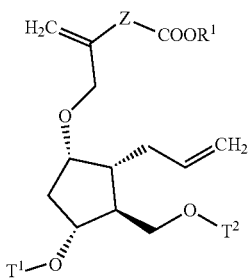

(D)

wherein, all symbols represent the same meanings as those described above;

step (iv): subjecting the compound represented by the general formula (D) obtained in the step (iii) to a metathesis reaction to produce a compound represented by the general formula (E):

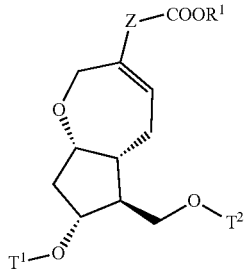

(E)

wherein, all symbols represent the same meanings as those described above;

step (v): subjecting the compound represented by the general formula (E) obtained in the step (iv) to an asymmetric reduction reaction to produce a compound represented by the general formula (F):

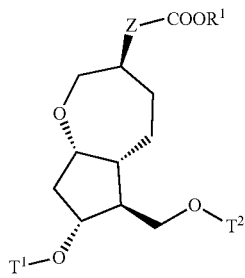

(F)

wherein, all symbols represent the same meanings as those described above; and step (vi): subjecting the compound represented by the general formula (F) obtained in the step (v) to a deprotection reaction to produce the compound represented by the general formula (G) described in the above [3] or a salt thereof;

[5] A method for producing the compound represented by the general formula (K) described in the above [1], the method comprising: producing the compound represented by the general formula (G) or a salt thereof from the compound represented by the general formula (A) according to the steps (i) to (vi) described in the above [4]; producing the compound represented by the general formula (I) or a salt thereof from the compound represented by the general formula (G) or a salt thereof according to the steps (vii) to (viii) described in the above [3]; and producing the compound represented by the general formula (K) according to the steps (ix) to (x) described the above [2];

[6] The method according to any one of the above [1] to [5], wherein $T^1$ is a p-phenybenzoyl group;

[7] The method according to any one of the above [4] to [6], wherein $T^2$ is a benzyl group;

[8] The method according to any one of the above [1], [2], [5], [6], and [7], wherein the compound represented by the general formula (K) is 2-propanyl 4-{(3S,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}butanoate;

[9] (3 aR,4S,5R,6aS)-4-[(benzyloxy)methyl]-2-hydroxy-hexahydro-2H-cyclopenta[b]furan-5-yl 4-biphenylcarboxylate;

[10] (1R,2S,3R,4S)-3-allyl-2-[(benzyloxy)methyl]-4-hydroxycyclopentyl 4-biphenylcarboxylate;

[11] 2-propanyl 5-(bromomethyl)-5-hexenoate;

[12] (1R,2S,3R,4S)-3-allyl-2-[(benzyloxy)methyl]-4-{[2-methylene-6-oxo-6-(2-propanyloxy)hexyl]oxy}cyclopentyl 4-biphenylcarboxylate;

[13] (5aR,6S,7R,8aS)-6-[(benzyloxy)methyl]-3-[4-oxo-4-(2-propanyloxy)butyl]-5,5a,6,7,8,8a-hexahydro-2H-cyclopenta[b]oxepin-7-yl 4-biphenylcarboxylate;

[14] (3S,5aR,6S,7R,8aS)-6-[(benzyloxy)methyl]-3-[4-oxo-4-(2-propanyloxy)butyl]octahydro-2H-cyclopenta[b]oxepin-7-yl 4-biphenylcarboxylate;

[15] (3 S,5aR,6R,7R,8aS)-6-[(1E)-4-(2,5-difluorophenoxy)-3-oxo-1-buten-1-yl]-3-[4-oxo-4-(2-propanyloxy)butyl]octahydro-2H-cyclopenta[b]oxepin-7-yl 4-biphenylcarboxylate; and

[16] (3S,5aR,6R,7R,8aS)-6-[(1E,3R)-4-(2,5-difluorophenoxy)-3-hydroxy-1-buten-1-yl]-3-[4-oxo-4-(2-propanyloxy)butyl]octahydro-2H-cyclopenta[b]oxepin-7-yl 4-biphenylcarboxylate;

and the like.

Advantageous Effects of Invention

According to the present invention, by changing the starting material and improving the metathesis reaction, the asymmetric reduction reaction and the like, the total number of steps can be reduced, the total reaction yield can be high, and the present compound can be stably supplied, and therefore, the present invention is an extremely useful production method from the viewpoint of industrial productivity of the present compound which is a drug substance for a medicine.

DESCRIPTION OF EMBODIMENTS

Hereinafter, the present invention will be described in detail.

In the present invention, the C1-6 alkyl group means a straight or branched C1-6 alkyl group such as methyl, ethyl, propyl, isopropyl, butyl, sec-butyl, tert-butyl, pentyl, isopentyl, tert-pentyl, neopentyl, and hexyl.

In the present invention, the C1-4 alkyl group means a straight or branched C1-4 alkyl group such as methyl, ethyl, propyl, isopropyl, butyl, sec-butyl, and tert-butyl.

In the present invention, the C1-4 alkoxy group means a straight or branched C1-4 alkoxy group such as methoxy, ethoxy, propoxy, isopropoxy, butoxy, isobutyloxy, and tert-butoxy.

In the present invention, the halogen atom means fluorine, chlorine, bromine, and iodine.

In the present invention, the C3-10 carbocycle means a C3-10 monocyclic or bicyclic carbocycle, a part or all of which may be saturated, and examples include cyclopropane, cyclobutane, cyclopentane, cyclohexane, cycloheptane, cyclooctane, cyclononane, cyclodecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, perhydroindane, naphthalene, dihydronaphthalene, tetrahydronaphthalene, perhydronaphthalene and the like.

In the present invention, the C3-7 carbocycle means a C3-7 monocyclic carbocycle, a part or all of which may be saturated, and examples include cyclopropane, cyclobutane, cyclopentane, cyclohexane, cycloheptane, cyclopentene, cyclohexene, cycloheptene, cyclopentadiene, cyclohexadiene, cycloheptadiene, benzene and the like.

In the present invention, the 3- to 10-membered heterocycle means a 3- to 10-membered monocyclic or bicyclic heterocycle, a part or all of which may be saturated, comprising 1 to 5 heteroatoms selected from an oxygen atom, a nitrogen atom and a sulfur atom, and examples include pyrrole, imidazole, triazole, tetrazole, pyrazole, pyridine, pyrazine, pyrimidine, pyridazine, azepine, diazepine, furan, pyran, oxepin, thiophene, thiopyran, thiepin, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepin, tetrahydrooxepin, perhydrooxepin, thiirane, thietane, dihydrothiophene, tetrahydrothiophene, dihydrothiopyran, tetrahydrothiopyran, dihydrothiepin, tetrahydrothiepin, perhydrothiepin, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, dioxolane, dioxane, dithiolane, dithiane, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, pyrrolopyridine, benzoxazole, benzothiazole, benzimidazole, chromene, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, tetrahydropyrrolopyridine, dihydrocinnoline, tetrahydrocinnoline, perhydrocinnoline, benzoxathian, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, and perhydrobenzimidazole.

In the present invention, the sulfur atom in A includes an oxidized sulfur atom, that is, —SO— or —SO$_2$— in addition to —S—.

In the present invention, the present compound means the compound represented by the following formula:

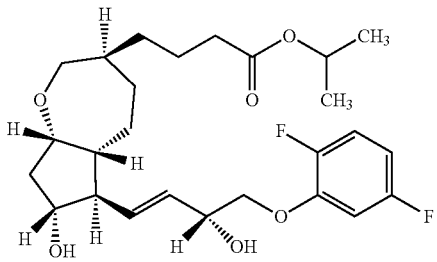 [SMILES: CC(C)OC(=O)CCC[C@H]1CC[C@@H]2[C@@H](/C=C/[C@@H](O)COc3cc(F)ccc3F)[C@H](O)C[C@@H]2OC1]

that is, 2-propanyl 4-{(3S,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}butanoate.

In the present invention, the step (i) means a step of subjecting a compound represented by the general formula (A):

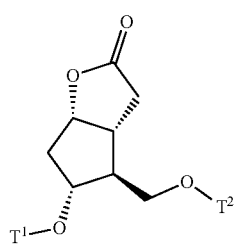

wherein, all symbols represent the same meanings as those described above, to a reduction reaction to produce a compound represented by the general formula (B):

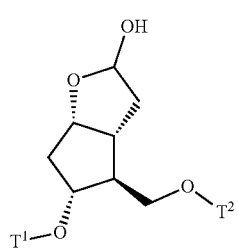

wherein, all symbols represent the same meanings as those described above, or a salt thereof.

The reduction reaction in the step (i) can be carried out, for example, in an organic solvent (for example, toluene, ethanol, tetrahydrofuran, hexane, methylene chloride and the like), in the presence of a reducing agent (for example, diisobutylaluminium hydride (DIBAL), lithium aluminium hydride, sodium borohydride and the like) at −78 to 80° C. Here, the organic solvent is preferably tetrahydrofuran, and the reducing agent is preferably DIBAL.

In the present invention, the step (ii) means a step of subjecting a compound represented by the general formula (B) obtained in the step (i) or a salt thereof to a reaction in an organic solvent, in the presence of a base, by using a Wittig reagent to produce a compound represented by the general formula (C):

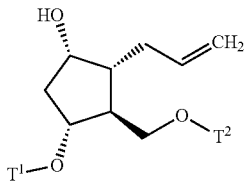

wherein, all symbols represent the same meanings as those described above, or a salt thereof.

Examples of the organic solvent in the step (ii) include anhydrous toluene, dimethoxyethane, tetrahydrofuran, 1,4-dioxane and the like, with tetrahydrofuran being preferred.

Examples of the base in the step (ii) include lithium hexamethyldisilazane (LHMDS), lithium diisopropylamide (LDA), butyllithium, potassium tert-butoxide, sodium hydride and the like, with potassium tert-butoxide being preferred.

Examples of the Wittig reagent in the step (ii) include methyltriphenylphosphonium bromide and the like.

In the present invention, the step (iii) means a step of subjecting a compound represented by the general formula (C) obtained in the step (ii), or a salt thereof and a compound represented by the general formula (a):

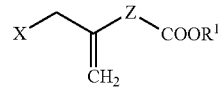

wherein, all symbols represent the same meanings as those described above, to an alkylation reaction to produce a compound represented by the general formula (D):

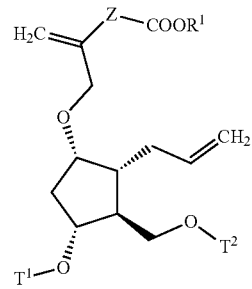

wherein, all symbols represent the same meanings as those described above.

The alkylation reaction in the step (iii) is known, and can be carried out, for example, by using a compound represented by the general formula (C) or a salt thereof and a compound represented by the general formula (a) in an organic solvent (for example, 1,3-dimethyl-3,4,5,6-tetrahydro-2(1H)-pyrimidinone (DMPU), N-methylpyrrolidone (NMP), hexamethylphosphoric triamide, dimethylformamide and the like), in the presence of a base (for example, sodium tert-butoxide, sodium hydride, lithium diisopropylamide (LDA), sodium hexamethyldisilazane and the like) at −78 to 80° C. Here, DMPU is preferably used as the organic solvent, and sodium tert-butoxide is preferably used as the base.

In the present invention, the step (iv) means a step of subjecting a compound represented by the general formula (D) obtained in the step (iii) to a metathesis reaction to produce a compound represented by the general formula (E):

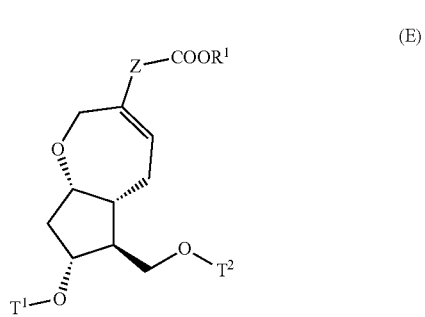

(E)

wherein, all symbols represent the same meanings as those described above.

The metathesis reaction in the step (iv) is known and can be carried out, for example, by using a metathesis catalyst (for example, 2,6-diisopropylphenylimido neophylidenemolybdenum(VI) bis(tert-butoxide), 2,6-diisopropylphenylimido neophylidenemolybdenum(VI) bis(hexafluoro-tert-butoxide), Umicore M2 (trade name) and the like) in an organic solvent (for example, toluene, methylene chloride, dichloroethane and the like) at a temperature of 20 to 110° C. Here, the organic solvent is preferably toluene, and the metathesis catalyst is preferably Umicore M2.

In the present invention, the step (v) means a step of subjecting a compound represented by the general formula (E) obtained in the step (iv) to an asymmetric reduction reaction to produce a compound represented by the general formula (F):

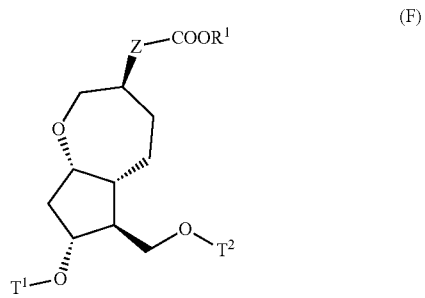

(F)

wherein, all symbols represent the same meanings as those described above.

The asymmetric reduction reaction in the step (v) is known, and can be carried out, for example, by using an iridium catalyst (for example, bis(cyclooctadiene)iridium(I) tetrakis[3,5-bis(trifluoromethyl)phenyl]borate and the like) and a ligand (for example, (S,S)-(4,5-dihydro-4-isopropyl-2-oxazolyl)-2-[di(1-naphthyl)phosphino]ferrocene and the like) in an organic solvent (for example, methylene chloride, dichloroethane, tetrahydrofuran, methanol and the like) at a temperature of 20 to 80° C. Here, the organic solvent is preferably methylene chloride, and preferable examples of the combination of the iridium catalyst and the ligand include a combination of tetrakis[3,5-bis(trifluoromethyl)phenyl]borate and (S,S)-(4,5-dihydro-4-isopropyl-2-oxazolyl)-2-[di(1-naphthyl)phosphino]ferrocene.

In the present invention, the step (vi) means a step of subjecting a compound represented by the general formula (F) obtained in the step (v) to a deprotection reaction to produce a compound represented by the general formula (G):

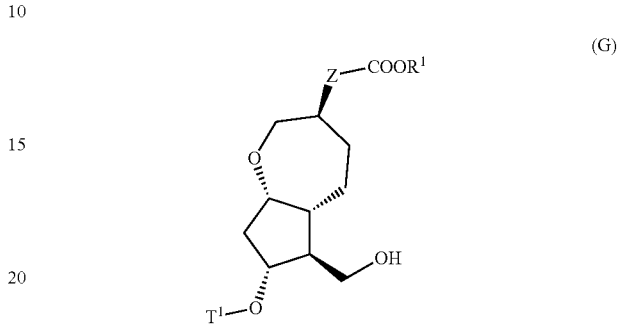

(G)

wherein, all symbols represent the same meanings as those described above, or a salt thereof.

In the step (vi), a deprotection reaction of a hydroxyl group is known, and examples include:
(1) a deprotection reaction under the basic condition,
(2) a deprotection reaction under the acidic condition,
(3) a deprotection reaction by hydrogenation degradation,
(4) a deprotection reaction of a silyl group,
(5) a deprotection reaction using a metal,
(6) a deprotection reaction using a metal complex, and the like.

To specifically describe these methods,
(1) The deprotection reaction under the basic condition is performed, for example, by using, a hydroxide of an alkali metal (sodium hydroxide, potassium hydroxide, lithium hydroxide and the like), a hydroxide of an alkaline earth metal (barium hydroxide, calcium hydroxide and the like), an alkoxide of an alkali metal (sodium methoxide, sodium ethoxide, lithium isopropoxide and the like), or a carbonate (sodium carbonate, potassium carbonate and the like), or an aqueous solution thereof, or a mixture thereof, in an organic solvent (methanol, ethanol, isopropanol, tetrahydrofuran, dioxane and the like) at a temperature of 0 to 80° C.

(2) The deprotection reaction under the acidic condition is performed, for example, in an organic solvent (dichloromethane, chloroform, dioxane, ethyl acetate, anisole and the like), in an organic acid (acetic acid, trifluoroacetic acid, methanesulfonic acid, p-tosic acid and the like), or an inorganic acid (hydrochloric acid, sulfuric acid and the like) or a mixture thereof (hydrogen bromide/acetic acid and the like) at a temperature of 0 to 100° C.

(3) The deprotection reaction by hydrogenation degradation is performed, for example, in a solvent (for example, ether-based solvent (for example, tetrahydrofuran, dioxane, dimethoxyethane, diethyl ether and the like), alcohol-based solvent (for example, methanol, ethanol and the like), benzene-based solvent (for example, benzene, toluene and the like), ketone-based solvent (for example, acetone, methyl ethyl ketone and the like), nitrile-based solvent (for example, acetonitrile and the like), amide-based solvent (for example, N,N-dimethylformamide and the like), water, ethyl acetate, isopropyl acetate, acetic acid or a mixed solvent of two or more of them and the like), in the presence of a catalyst (for example, palladium on carbon, palladium black, palladium hydroxide on carbon, platinum oxide, Raney nickel and the like), under the hydrogen atmosphere at a normal pressure or under pressure, or in the presence of ammonium formate, at 0 to 200° C.

(4) The deprotection reaction of a silyl group is performed, for example, in an organic solvent which is miscible with water (tetrahydrofuran, acetonitrile and the like), by using tetrabutylammonium fluoride, at a temperature of 0 to 40° C.

(5) The deprotection reaction by using a metal is performed, for example, in an acidic solvent (acetic acid, a buffer of pH 4.2 to 7.2, or a mixed solution of any of those solutions and an organic solvent such as tetrahydrofuran), in the presence of a zinc powder, if necessary, while an ultrasound is applied, at a temperature of 0 to 40° C.

(6) The deprotection reaction by using a metal complex is performed, for example, in an organic solvent (dichloromethane, dimethylformamide, tetrahydrofuran, ethyl acetate, acetonitrile, dioxane, ethanol and the like), water or a mixed solvent thereof, in the presence of a trap reagent (tributyltin hydride, triethylsilane, dimedone, morpholine, diethylamine, pyrrolidine and the like), an organic acid (acetic acid, formic acid, 2-ethyhexanoic acid and the like) and/or an organic acid salt (sodium 2-ethylhexanoate, potassium 2-ethylhexanoate and the like), in the presence or absence of a phosphine-based reagent (triphenylphosphine and the like), by using a metal complex (tetrakis(triphenylphosphine)palladium(0), bis(triphenylphosphine)palladium(II) dichloride, palladium(II) acetate, chlorotris(triphenylphosphine)rhodium(I) and the like) at a temperature of 0 to 40° C.

In the step (vi), when $T^2$ is a benzyl group, it is preferable to use isopropyl acetate as a solvent, and palladium on carbon as a catalyst, and to perform the deprotection reaction under the hydrogen atmosphere under pressure.

Additionally, in addition to the above reactions, the deprotection reaction can be performed, for example, by the method described in T. W. Greene, Protective Groups in Organic Synthesis, Wiley, New York, 1999.

In the present invention, the step (vii) means a step of subjecting a compound represented by the general formula (G) obtained in the step (vi), or a salt thereof to an oxidation reaction to produce a compound represented by the general formula (H):

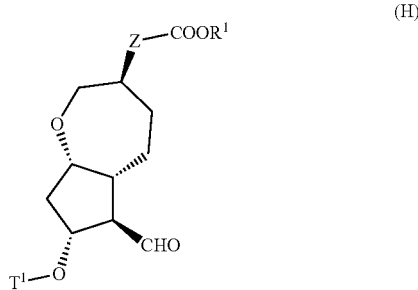

wherein, all symbols represent the same meanings as those described above.

The oxidation reaction in the step (vii) is known, and is performed, for example, by a reaction with the alcohol compound at −78 to 80° C. in a solvent (for example, an organic solvent (for example, chloroform, methylene chloride, ethyl acetate, isopropyl acetate, tetrahydrofuran, dimethylformamide and the like), water, or a mixed solvent of two or more of them and the like), in the presence of a combination of an activating agent (for example, a combination of a diimide compound (for example, 1-(3-dimethylaminopropyl)-3-ethylcarbodiimide hydrochloride, dicyclohexylcarbodiimide and the like) and an acid (for example, dichloroacetic acid, trifluoroacetic acid, acetic acid and the like), or pyridine sulfur trioxide complex, oxalyl chloride and the like) and an oxidizing agent (for example, dimethyl sulfoxide and the like), or a combination of an activating agent (for example, 2,2,6,6-tetramethylpiperidine-1-oxy radical, 2-hydroxy-2-azaadamantane and the like) and an oxidizing agent (for example, a sodium hypochlorite aqueous solution, trichloroisocyanuric acid and the like) and the like. Here, as the oxidation reaction in the step (vii), it is preferable to use a combination of a combination of 1-(3-dimethylaminopropyl)-3-ethylcarbodiimide hydrochloride and dichloroacetic acid, and dimethyl sulfoxide as an oxidizing agent.

In the present invention, the step (viii) means a step of subjecting a compound represented by the general formula (H) obtained in the step (vii) and a compound represented by the general formula (b):

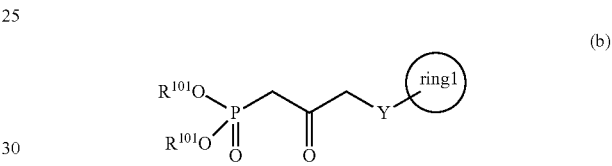

wherein, all symbols represent the same meanings as those described above, to a reaction in an organic solvent, or in water, or in a mixed solution thereof, in the presence of a base, in the presence or absence of an additive to produce a compound represented by the general formula (I):

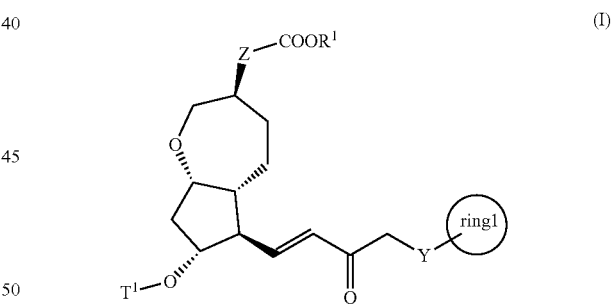

wherein, all symbols represent the same meanings as those described above, or a salt thereof.

Examples of the organic solvent in the step (viii) include tetrahydrofuran (THF), dimethylformamide (DMF), dimethoxyethane (DME), dioxane, acetonitrile, ethanol, methylene chloride, isopropanol and the like. In the step (viii), a mixed solution of an organic solvent and water is preferable, and a mixed solution of tetrahydrofuran, isopropanol and water is more preferable.

Examples of the base in the step (viii) include sodium hydride, sodium hydroxide, potassium hydroxide, potassium phosphate, potassium tert-butoxide, potassium carbonate, a tertiary amine (for example, triethylamine and the like) and the like, and it is preferable to use a combination of triethylamine and lithium chloride as an additive thereof.

In the present invention, the step (ix) means a step of subjecting a compound represented by the general formula (I) obtained in the step (viii), or a salt thereof to an asymmetric reduction reaction to produce a compound represented by the general formula (J):

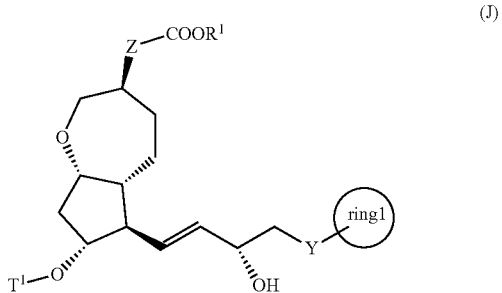

wherein, all symbols represent the same meanings as those described above, or a salt thereof.

The asymmetric reduction reaction in the step (ix) is known, and is performed, for example, in an organic solvent (for example, THF, DME, toluene, methylene chloride, diethyl ether, dioxane and the like), by using an asymmetric reducing agent (for example, chlorobis(2,6,6-trimethylbicyclo[3.1.1]heptan-3-yl)borane and the like), or a combination of a chiral auxiliary and a reducing agent ((R)-2-methyl-CBS-oxazaborolidine and a boron hydride-tetrahydrofuran complex or a borane dimethyl sulfide complex, (S)-(−)-binaphthol and lithium aluminium hydride and the like), at a temperature of −100 to 50° C. Here, toluene is preferable as the organic solvent, and chlorobis(2,6,6-trimethylbicyclo[3.1.1]heptan-3-yl)borane is preferable as the asymmetric reducing agent.

In the present invention, the step (x) means a step of subjecting a compound represented by the general formula (J) obtained in the step (ix), or a salt thereof to a deprotection reaction to produce a compound represented by the general formula (K):

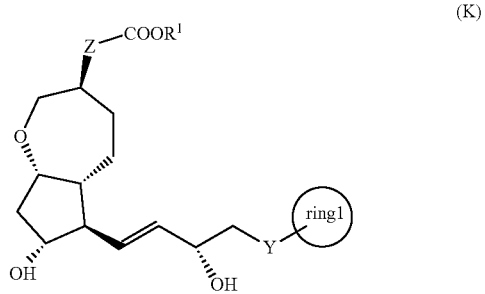

wherein, all symbols represent the same meanings as those described above.

The deprotection reaction of a hydroxyl group in the step (x) is known, and the deprotection reaction can be performed in the same manner as described in the step (vi).

In the step (x), when $T^1$ is a p-phenybenzoyl group, the deprotection reaction under the basic condition performed by using lithium isopropoxide as the alkoxide of the alkali metal and THF, isopropanol as the organic solvent is preferable.

The production method according to the present invention includes all methods for producing the present compound or an arbitrary intermediate compound for manufacturing the same by carrying out one or two or more consecutive steps out of the above steps (i) to (x), but includes in particular the following production methods.

(1) The method for producing a compound represented by the general formula (G), or a salt thereof, by using the above-described compound represented by the general formula (A) and sequentially carrying out the above described step (i)→step (ii)→step (iii)→step (iv)→step (v)→step (vi).

(2) The method for producing a compound represented by the general formula (I), or a salt thereof, by using the above-described compound represented by the general formula (G), or a salt thereof and sequentially carrying out the above described step (vii)→step (viii).

(3) The method for producing a compound represented by the general formula (K) including the present compound, by using the above-described compound represented by the general formula (I), or a salt thereof and sequentially carrying out the above described step (ix)→step (x).

(4) The method for producing a compound represented by the general formula (K) including the present compound, by using the above-described compound represented by the general formula (A), and sequentially carrying out the above described step (i)→step (x).

Here, any of arbitrary intermediate compounds for the manufacture represented by the general formulae (B), (C), (G), (I) and (J) may be, if necessary, converted to a salt according to a known method.

In the present invention, a compound represented by the general formula (A), and a compound represented by the general formula (a) or the general formula (b) used as starting raw materials are known, or can be easily produced by a known method.

In the present invention, $T^1$ is preferably a p-phenybenzoyl group.

In the present invention, $T^2$ is preferably a benzyl group.

In the present invention, it is preferable that $T^1$ and $T^2$ are different protecting groups.

In the present invention, the ring 1 is preferably a C3-7 carbocycle, and is more preferably a benzene or cyclohexane ring. Here, the substituent of the ring 1 is preferably a C1-4 alkyl group, a C1-4 alkoxy group, $CF_3$, $OCF_3$ or a halogen atom, and is more preferably a C1-4 alkyl group, $CF_3$, $OCF_3$ or a halogen atom.

In the present invention, any intermediate which can be produced by each of the steps is preferable, and a compound represented by the general formula (B), a compound represented by the general formula (C), a compound represented by the general formula (a), a compound represented by the general formula (D), a compound represented by the general formula (E), a compound represented by the general formula (F), a compound represented by the general formula (I), and a compound represented by the general formula (J) are more preferable. As a compound represented by the general formula (B), (3aR,4S,5R,6aS)-4-[(benzyloxy)methyl]-2-hydroxyhexahydro-2H-cyclopenta[b]furan-5-yl 4-biphenylcarboxylate is preferable. As a compound represented by the general formula (C), (1R,2S,3R,4S)-3-allyl-2-[(benzyloxy)methyl]-4-hydroxycyclopentyl 4-biphenylcarboxylate is preferable. As a compound represented by the general formula (a), 2-propanyl 5-(bromomethyl)-5-hexenoate is preferable. As a compound represented by the general formula (D), (1R,2S,3R,4S)-3-allyl-2-[(benzyloxy)methyl]-4-{[2-methylene-6-oxo-6-(2-propanyloxy)hexyl]oxy}cyclopentyl 4-biphenylcarboxylate is preferable. As a compound represented by the general formula (E), (5aR,6S,7R,8aS)-6-[(benzyloxy)methyl]-3-[4-oxo-4-(2-propanyloxy)butyl]-5,5a,6,7, 8,8a-hexahydro-2H-cyclopenta[b]oxepin-7-yl 4-biphenylcarboxylate is preferable. As a compound represented by the general formula (F), (3S,5aR,6S,7R,8aS)-6-[(benzyloxy)methyl]-3-[4-oxo-4-(2-propanyloxy)butyl]octahydro-2H-cyclopenta[b]oxepin-7-yl 4-biphenylcarboxylate is preferable. As a compound represented by the general formula (I), (3S,5aR,6R,7R,8aS)-6-[(1E)-4-(2,5-difluorophenoxy)-3-oxo-1-buten-1-yl]-3-[4-oxo-4-(2-propanyloxy)butyl]octahydro-2H-cyclopenta[b]oxepin-7-yl 4-biphenylcarboxylate is preferable. As a compound represented by the general formula (J), (3S,5aR,6R,7R,8aS)-6-[(1E,3R)-4-(2,5-difluorophenoxy)-3-hydroxy-1-buten-1-yl]-3-[4-oxo-4-(2-propanyloxy)butyl]octahydro-2H-cyclopenta[b]oxepin-7-yl 4-biphenylcarboxylate is preferable. In addition, as a compound represented by the general formula (K), 2-propanyl 4-{(3S,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}butanoate is preferable.

The production method according to the present invention is not limited to the above-described present compound, and can be also applied to, for example, examples described in Patent Literature 1. For example, Examples 16 (1) to 16 (4), Examples 16 (9) to 16 (42), Examples 18 (1) to 18 (4), Example 28, Examples 28 (1) to 28 (17), Example 31, Example 40, Example 46, Examples 48 (1) to 48 (2), and Example 97 described in Patent Literature 1 are encompassed in a compound represented by the general formula (K) according to the present invention, and therefore, as apparent to those skilled in the art, the production method according to the present invention can be applied to the group of compounds.

In the present invention, unless otherwise indicated, as is apparent to those skilled in the art, a symbol:

represents that a group is bound to another side of a paper plane (i.e. α-configuration), a symbol:

represents that a group is bound to a front side of a paper plane (i.e. β-configuration), and a symbol:

represents α configuration, β configuration or a mixture thereof at an arbitrary ratio.

In the present invention, a pharmaceutically acceptable salt is preferable as a salt. Examples of the pharmaceutically acceptable salt include a salt of an alkali metal (potassium, sodium and the like), a salt of an alkaline earth metal (calcium, magnesium and the like), an ammonium salt, a salt of a pharmaceutically acceptable organic amine (triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine and the like), an acid adduct salt (an inorganic acid salt (hydrochloride, hydrobromide, hydroiodide, sulfate, phosphate, nitrate and the like), an organic acid salt (acetate, trifluoroacetate, lactate, tartrate, oxalate, fumarate, maleate, benzoate, citrate, methanesulfonate, ethanesulfonate, benzenesulphonate, toluenesulfonate, isethionate, glucuronate, gluconate and the like) and the like.

EXAMPLES

Hereinafter, the present invention will be described in detail by examples, but the present invention is not limited thereto.

A solvent in parentheses shown in a place of separation by chromatography and TLC indicates an eluting solvent or a developing solvent used, and a ratio represents a volumetric ratio.

NMR data are data of $^1$H-NMR unless otherwise indicated.

A solvent in measurement is indicated in parentheses shown at a place of NMR.

A compound name used in the present specification was generally named by using a computer program, ACD/Name (registered trademark) of Advanced Chemistry Development, which performs naming according to a rule of IUPAC, or according to IUPAC nomenclature.

Example 1: 2-propanyl 5-({[dimethyl(2-methyl-2-propanyl)silyl]oxy}methyl)-5-hexenoate

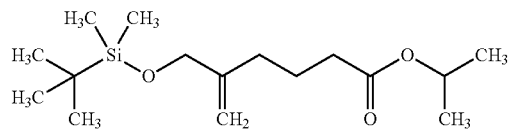

A zinc powder (131 g) was suspended in dimethylacetamide (934 g), and to the mixture, iodine (28.3 g) was added, and the mixture was stirred at room temperature. The mixture was heated to 70° C., isopropyl 4-bromobutyrate (234 g) (see The Journal of Organic Chemistry, Vol. 70, pages 1227-1236, 2005) was added to the mixture and the mixture was washed with dimethylacetamide (51 g). After stirring for 2 hours, the mixture was cooled to room temperature, [(2-bromo-2-propen-1-yl)oxy](dimethyl)(2-methyl-2-propanyl)silane (168 g) (see Organic Letters, Vol. 18, pages 1904-1907, 2016), and dichlorobis(triphenylphosphine)palladium (4.7 g) were added to the mixture and a reaction solution was washed with dimethylacetamide (51 g). After stirring at 50° C. for 12 hours, the above reaction solution was added to a mixture of ammonium chloride (115 g) and water (504 g). Insoluble matters were filtrated through celite, and the residue was washed with isopropyl acetate (252 g). The filtrate was extracted with methyl tert-butyl ether (hereinafter abbreviated as MTBE) (65 g), isopropyl acetate (126 g) was added to the organic layer and the organic layer was washed twice with water (128 g). The organic layer was concentrated under reduced pressure to give the title compound (218 g) having the following physical properties.

TLC: Rf 0.60 (hexane:ethyl acetate=9:1);

$^1$H-NMR (CDCl$_3$): δ 5.06-5.04, 5.04-4.96, 4.83, 4.06, 2.28, 2.07-2.02, 1.82-1.72, 1.23, 0.91, 0.07.

Example 2: 2-propanyl 5-(hydroxymethyl)-5-hexenoate

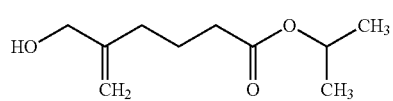

The compound produced in Example 1 (217 g) was dissolved in isopropanol (282 g), 2 M hydrochloric acid (36 mL) was added to the solution, and the solution was stirred at room temperature for 3 hours. Water (130 g), sodium hydrogen carbonate (7 g), MTBE (65 g) and heptane (65 g) were added to the reaction solution and the liquid mixture was separated. The organic layer was washed with water (130 g), and 18% brine (120 g). The organic layer was dried over magnesium sulfate, and thereafter, was filtrated. The solvent in the filtrate was distilled off, and the residue was purified by silica gel column chromatography to give the title compound (71.8 g) having the following physical properties.

TLC: Rf 0.33 (hexane:ethyl acetate=2:1);
$^1$H-NMR (CDCl$_3$): δ 5.06-5.04, 5.04-4.94, 4.90-4.88, 4.09, 2.30, 2.11, 1.80, 1.53, 1.23.

Example 3: 2-propanyl 5-(bromomethyl)-5-hexenoate

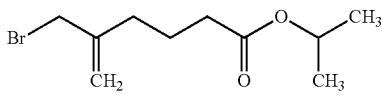

The compound produced in Example 2 (20 g) and triethylamine (13 g) were dissolved in toluene (160 g), and methanesulfonyl chloride (12.9 g) was added dropwise to the solution under cooling with ice. After stirring for 30 minutes, water (50 g) was added to the solution, the liquid mixture was separated, and the organic layer was washed with water (50 g) and 18% brine (25 g). The organic layer was dried over magnesium sulfate, and thereafter, was filtrated to give a filtrate containing 2-propanyl 5-{[(methylsulfonyl)oxy]methyl}-5-hexenoate. Lithium bromide (11.2 g) was added to the filtrate, and the mixture was stirred at room temperature for 15 hours. Water (50 g) was added to the mixture, the liquid mixture was separated, and the organic layer was washed with water (30 g) and 18% brine (25 g). The organic layer was dried over magnesium sulfate, and thereafter, was filtrated. The solvent in the filtrate was distilled off, and the residue was purified by distillation under reduced pressure to give the title compound (18.7 g) having the following physical properties.

TLC: Rf 0.52 (hexane:ethyl acetate=6:1);
$^1$H-NMR (CDCl$_3$): δ 5.19, 5.05-4.97, 3.96, 2.33-2.23, 1.86-1.75, 1.24.

Example A:
2,2-bis(hydroxymethyl)cyclopentan-1-one

Cyclopentanone (50 g) (CAS Registry Number: 120-92-3) was placed in a reaction vessel, the internal temperature was cooled to 5° C. or lower, and potassium carbonate (12.2 g) was added thereto. Subsequently, formalin (28% solution) (119.7 g) was added dropwise over 1 hour at the same temperature and the mixture was stirred for 2 hours. The reaction solution was extracted three times with ethyl acetate (250 mL). The obtained organic layer was dried over magnesium sulfate, and thereafter, concentrated under reduced pressure to give the title compound (21.9 g) having the following physical properties.
$^1$H-NMR (CDCl$_3$): δ 4.27-4.19, 2.71-2.59, 1.92-1.83, 1.83-1.71.

Example B:
(2-oxocyclopentane-1,1-diyl)bis(methylene) dimethanesulfonate

Ethyl acetate (110 mL) and the compound produced in Example A (21.9 g) were placed in a reaction vessel, the internal temperature was cooled to 10° C. or lower, and triethylamine (33.4 g) was added thereto. Subsequently, methanesulfonyl chloride (37.8 g) was added dropwise to the mixture at the same temperature over 1 hour and the mixture was stirred for 30 minutes. A solution of sodium hydrogen carbonate (2.2 g) in water (66 mL) was added to the reaction solution, and the mixture was extracted with ethyl acetate (110 mL). The obtained organic layer was washed with water, was dried over magnesium sulfate and then was concentrated under reduced pressure to give the title compound (39.1 g) having the following physical properties.
$^1$H-NMR (CDCl$_3$): δ 4.24, 4.21, 3.93, 3.39, 2.20, 2.09-1.99.

Example C:
2,2-bis(bromomethyl)cyclopentan-1-one

Methyl ethyl ketone (196 mL) and the compound produced in Example B (39.1 g) were placed in a reaction vessel, followed by the addition of lithium bromide (45.8 g), the temperature was raised to an internal temperature of 80 to 90° C. and the mixture was stirred for 5 hours. The reaction solution was cooled to room temperature, was washed twice with water (156 mL), was dried over magnesium sulfate and then was concentrated under reduced pressure to give the title compound (29.3 g) having the following physical properties.
$^1$H-NMR (CDCl$_3$): δ 3.51, 3.47, 2.38, 2.27, 2.04.

Example 3-1:2-propanyl 5-(bromomethyl)-5-hexenoate

Isopropyl alcohol (146 mL) and the compound produced in Example C (29.2 g) were placed in a reaction vessel, and the internal temperature was cooled to 10° C. or lower. Subsequently, a solution of potassium tert-butoxide (30.3 g) in isopropyl alcohol (292 mL) was added dropwise thereto over 1 hour. The mixture was stirred at the same temperature for 30 minutes, acetic acid (13.0 g) was added dropwise to the mixture, and the mixture was diluted with toluene (204 mL). The reaction solution was washed with water (146 mL) and a solution of sodium hydrogen carbonate (18.1 g) in water (146 mL), followed by washing twice with water (146 mL), the solution was dried over magnesium sulfate and then was concentrated under reduced pressure. The obtained residue was distilled under reduced pressure to give the title compound (25.0 g).

Example D: 2-propanyl 6-hydroxyhexanoate

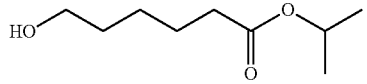

Isopropyl alcohol (150 mL) was placed in a reaction vessel, the internal temperature was cooled to 10° C. or lower, and sulfuric acid (0.26 g) was added thereto. Subsequently, a solution of ε-caprolactone (30 g) (CAS Registry Number: 502-44-3) in isopropyl alcohol (150 mL) was added dropwise thereto at the same temperature over 1 hour and 30 minutes. A saturated sodium hydrogen carbonate aqueous solution (30 mL) was added to the reaction solution, and the mixture was concentrated under reduced pressure.

The obtained residue was distilled under reduced pressure to give the title compound (26.3 g) having the following physical properties.
¹H-NMR (CDCl₃): δ 5.01, 3.63, 2.29, 1.70-1.52, 1.45-1.35, 1.23.

Example E: 2-propanyl 6-oxohexanoate

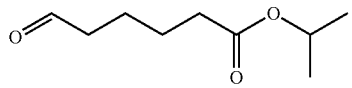

Dichloromethane (25 mL), water (25 mL) and the compound produced in Example D (5.0 g) were placed in a reaction vessel, and the mixture was cooled to an internal temperature of 5° C. or lower. Subsequently, potassium bromide (45.3 mg), sodium hydrogen carbonate (1.2 g) and 2,2,6,6-tetramethylpiperidine 1-oxyl (345.1 mg) were added thereto. At the same temperature, a sodium hypochlorite aqueous solution (available chlorine 4.8%) (153.6 g) was added dropwise thereto over 30 minutes. The organic layer in the reaction solution was preparatively isolated and the aqueous layer was extracted twice with dichloromethane (50 mL). The obtained organic layers were combined, washed with water (50 mL) and concentrated under reduced pressure. The obtained residue was distilled under reduced pressure to give the title compound (2.5 g) having the following physical properties. ¹H-NMR (CDCl₃): δ 9.78, 5.01, 2.54-2.40, 2.34-2.24, 2.30, 1.67, 1.23.

Example 2-1: 2-propanyl 5-(hydroxymethyl)-5-hexenoate

Isopropyl alcohol (2 mL), the compound produced in Example E (1.0 g), formalin (37% solution) (0.47 g) and diethylamine hydrochloride (63 mg) were placed in a reaction vessel, the internal temperature was raised to 50° C., and the mixture was stirred for 1 hour. At the same temperature, diethylamine hydrochloride (573 mg) was added thereto and the mixture was stirred for 4 hours. The reaction solution was cooled to room temperature, water (10 mL) was added to the reaction solution, and the mixture was extracted twice with MTBE (10 mL). The obtained organic layer was washed with water (10 mL) and concentrated under reduced pressure to give a residue containing 2-propanyl 5-formyl-5-hexenoate. THF (1 mL) was added to the residue, and the mixture was cooled to an internal temperature of 5° C. or lower. At the same temperature, sodium borohydride (219.4 mg) was added to the mixture, and methanol (1 mL) was added dropwise to the mixture. After stirring at the same temperature for 30 minutes, water (5 mL) was added to the mixture and the mixture was extracted three times with ethyl acetate (5 mL). The organic layers were combined, concentrated under reduced pressure, and the obtained residue was purified by silica gel column chromatography (n-hexane: ethyl acetate=3:1) to give the title compound (368.1 mg).

Example 3-2: 2-propanyl 5-(bromomethyl)-5-hexenoate

Using the compound produced in Example 2-1 instead of the compound produced in Example 2, the title compound was obtained by subjecting the compound to the operation having the same purpose as that of Example 3.

Example 4: (3 aR,4S,5R,6aS)-4-[(benzyloxy)methyl]-2-hydroxyhexahydro-2H-cyclopenta[b]furan-5-yl 4-biphenylcarboxylate

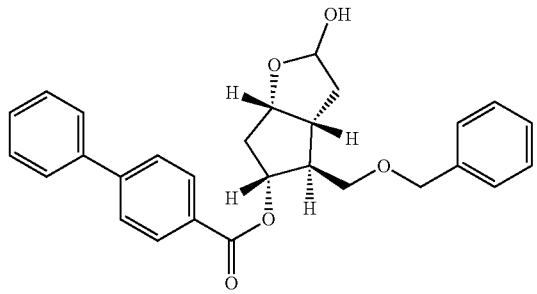

A solution of (3 aR,4S,5R,6aS)-4-[(benzyloxy)methyl]-2-oxohexahydro-2H-cyclopenta[b]furan-5-yl 4-phenylbenzoate (70.0 g) (CAS Registry Number: 31752-98-4) (Shanghai Julong Pharmaceutical R&D Co. Ltd.) in THF (350 mL) was cooled to −65° C. and 1 M isobutylaluminium hydride-toluene solution (190 mL) was added thereto at −55° C. or lower, and the reaction mixture was washed with THF (35 mL). The reaction mixture was stirred at −65° C. for 1 hour. Potassium sodium tartrate tetrahydrate (178 g) was dissolved in water (280 mL) in another reaction vessel and ethyl acetate (350 mL) was added thereto. The above reaction mixture was added to the mixture at 40° C. or lower and the mixture was washed with THF (35 mL). After stirring at 30° C. for 1 hour, the liquid mixture was separated. The organic layer was washed with 20% brine (140 mL), dried over magnesium sulfate, and then filtrated. The solvent in the filtrate was distilled off, the residue was suspended in a mixed solution of ethyl acetate (210 mL) and heptane (210 mL), and the suspension was stirred at room temperature for 30 minutes. The obtained crystals were collected by filtration and washed with a mixed solution of ethyl acetate (70 mL) and heptane (70 mL). By drying under reduced pressure at 50° C., the title compound (63.7 g) having the following physical properties was obtained.
¹H-NMR (CDCl₃): δ 8.05, 7.65-7.60, 7.49-7.45, 7.41-7.38, 7.32-7.24, 5.72, 5.33, 4.80, 4.52, 3.52, 2.78, 2.55, 2.48, 2.35, 2.24, 2.16-2.06.

Example 5: (1R,2S,3R,4S)-3-allyl-2-[(benzyloxy)methyl]-4-hydroxycyclopentyl 4-biphenylcarboxylate

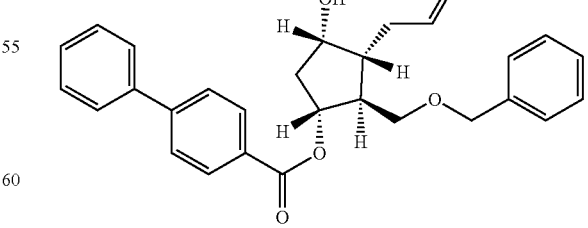

Methyltriphenylphosphonium bromide (63.9 g) was added to a solution of potassium tert-butoxide (16.3 g) in THF (550 mL) and the mixture was washed with THF (61 mL). A solution of the compound produced in Example 4 (61.4 g) in THF (370 mL) was added to the mixture at −15°

C. or lower, and the mixture was stirred for 1 hour. 0.5 M Hydrochloric acid (250 mL) and ethyl acetate (210 mL) were placed in a separate reaction vessel, the above reaction mixture was added thereto at 30° C. or lower and the mixture was washed with ethyl acetate (31 mL). The liquid mixture was separated, and the organic layer was washed sequentially with 5% sodium bicarbonate aqueous solution (250 mL) and 20% brine (120 mL). The organic layer was dried over magnesium sulfate, and thereafter, was filtrated. The solvent in the filtrate was distilled off, and the obtained residue was purified by silica gel column chromatography (heptane:ethyl acetate=8:1). Methanol (490 mL) was added to the obtained solid, and the mixture was stirred at 40° C. for 15 minutes. The mixture was filtrated, and washing with methanol (430 mL) was performed at 40° C. After cooling the filtrate to room temperature, water (61 mL) was added thereto. Seed crystals were added to precipitate crystals, and water (550 mL) was added thereto and the crystals were aged at room temperature for 1 hour. The obtained crystals were collected by filtration and washed with a mixed solution of methanol (180 mL) and water (120 mL). By drying under reduced pressure at 60° C., the title compound (57.1 g) having the following physical properties was obtained.

TLC: Rf 0.50 (hexane:ethyl acetate=3:1);

$^1$H-NMR (CDCl$_3$): δ 8.09, 7.68-7.60, 7.48-7.44, 7.42-7.37, 7.35-7.24, 5.89, 5.41, 5.13, 5.03, 4.58, 4.50, 4.29, 3.75, 3.56, 2.42-2.26, 2.02-1.93, 1.69.

Example 6: (1R,2S,3R,4S)-3-allyl-2-[(benzyloxy)methyl]-4-{[2-methylene-6-oxo-6-(2-propanyloxy)hexyl]oxy}cyclopentyl 4-biphenylcarboxylate

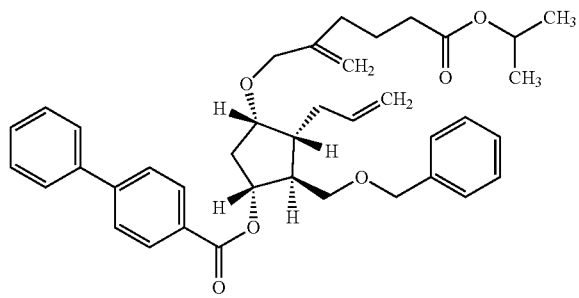 [SMILES: C=CC[C@@H]1[C@@H](COCc2ccccc2)[C@H](OC(=O)c2ccc(-c3ccccc3)cc2)C[C@@H]1OCC(=C)CCCC(=O)OC(C)C]

To a solution of the compound produced in Example 5 (70.0 g) in 1,3-dimethyl-3,4,5,6-tetrahydro-2(1H)-pyrimidinone (hereinafter abbreviated as DMPU) (280 mL), the compound produced in Example 3 (78.8 g) (here, the compound produced in Example 3-1 or Example 3-2 may be used) was added and the mixture was washed with DMPU (70 mL). The mixture was cooled to −25° C., a solution of sodium tert-butoxide (38.0 g) in DMPU (280 mL) was added thereto and the mixture was stirred for 1 hour. 1 M Hydrochloric acid (350 mL) and MTBE (560 mL) were placed in a separate reaction vessel, the above reaction mixture was added thereto at 30° C. or lower and the mixture was washed with MTBE (70 mL). The liquid mixture was separated and the aqueous layer was re-extracted with MTBE (350 mL). The organic layers were combined, washed with MTBE (70 mL) and washed sequentially with 5% sodium bicarbonate aqueous solution (140 mL) and 20% brine (140 mL). The organic layer was dried over magnesium sulfate, and thereafter, was filtrated. The solvent in the filtrate was distilled off, and the obtained residue was purified by silica gel column chromatography (heptane:ethyl acetate=20:1) to give the title compound (91.4 g) having the following physical properties.

TLC: Rf 0.47 (hexane:ethyl acetate=5:1);

$^1$H-NMR (CDCl$_3$): δ 8.09, 7.65-7.61, 7.48-7.37, 7.31-7.25, 5.84, 5.40, 5.10-4.87, 4.58, 4.49, 3.96, 3.88, 3.78-3.70, 3.56, 2.46, 2.35, 2.26-1.97, 1.76, 1.19.

Example 7: (5aR,6S,7R,8aS)-6-[(benzyloxy)methyl]-3-[4-oxo-4-(2-propanyloxy)butyl]-5,5a,6,7,8,8a-hexahydro-2H-cyclopenta[b]oxepin-7-yl 4-biphenylcarboxylate

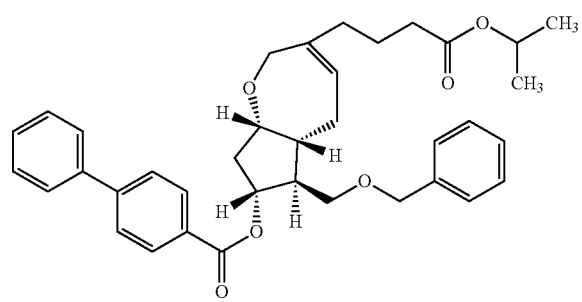 [SMILES: CC(C)OC(=O)CCCC1=CC[C@@H]2[C@@H](COCc3ccccc3)[C@H](OC(=O)c3ccc(-c4ccccc4)cc3)C[C@@H]2OC1]

Umicore M2 (trade name) (513 mg) (CAS registry number: 536724-67-1) was added to a toluene (450 mL) solution of the compound produced in Example 6 (66.0 g) and the mixture was washed with toluene (13 mL). After heating at 80° C. and stirring for 1 hour, the solvent was distilled off. The obtained residue was purified by silica gel column chromatography (heptane:ethyl acetate=20:1→10:1) to give the title compound (53.6 g) having the following physical properties.

TLC: Rf 0.57 (hexane:ethyl acetate=3:1);

$^1$H-NMR (CDCl$_3$): δ 8.08, 7.65-7.61, 7.49-7.37, 7.28-7.20, 5.50, 5.19, 5.01, 4.50, 4.38, 4.15-4.02, 3.52, 2.75-2.63, 2.37, 2.26, 2.20, 2.04, 1.92-1.83, 1.74-1.66, 1.23.

Example 8: (3S,5aR,6S,7R,8aS)-6-[(benzyloxy)methyl]-3-[4-oxo-4-(2-propanyloxy)butyl]octahydro-2H-cyclopenta[b]oxepin-7-yl 4-biphenylcarboxylate

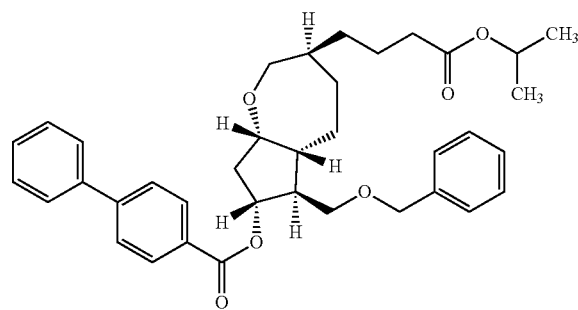 [SMILES: CC(C)OC(=O)CCC[C@H]1CC[C@@H]2[C@@H](COCc3ccccc3)[C@H](OC(=O)c3ccc(-c4ccccc4)cc3)C[C@@H]2OC1]

Bis(cyclooctadiene)iridium(I) tetrakis[3,5-bis(trifluoromethyl)phenyl]borate (3.37 g) (CAS Registry Number: 666826-16-0) and (S,S)-(4,5-dihydro-4-isopropyl-2-oxazolyl)-2-[di(1-naphthyl)phosphino]ferrocene (1.77 g) (CAS Registry Number: 950201-43-1) were dissolved in methylene chloride (410 mL), and the solution was stirred at room temperature for 30 minutes. A solution of the compound produced in Example 7 (51.4 g) in methylene chloride (51 mL) was added thereto at room temperature, and the mixture was washed with methylene chloride (51 mL). After stirring at room temperature for 3 hours under pressurized hydrogen at 5 atmospheric pressure, the solvent was distilled off. The obtained residue was purified by silica gel column chromatography (heptane:ethyl acetate=9:1) to give the title compound (50.1 g) having the following physical properties.

TLC: Rf 0.57 (hexane:ethyl acetate=3:1);

$^1$H-NMR (CDCl$_3$): δ 8.07, 7.65-7.61, 7.49-7.38, 7.24-7.21, 5.17, 5.00, 4.49, 4.10-3.99, 3.53, 2.97, 2.69, 2.25, 2.16, 2.04, 1.98-1.76, 1.73-1.59, 1.23, 1.19-1.03.

Example 9: (3S,5aR,6S,7R,8aS)-6-(hydroxymethyl)-3-[4-oxo-4-(2-propanyloxy)butyl]octahydro-2H-cyclopenta[b]oxepin-7-yl 4-biphenylcarboxylate

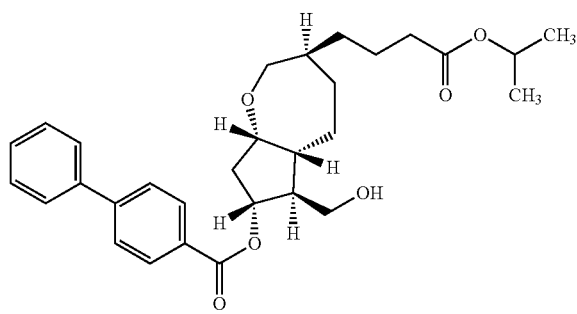 [SMILES: CC(C)OC(=O)CCC[C@H]1CC[C@@H]2[C@@H](CO)[C@H](OC(=O)c3ccc(-c4ccccc4)cc3)C[C@@H]2OC1]

20% Palladium hydroxide on carbon (water content 50%, 1.47 g) was added to a solution of the compound produced in Example 8 (14.7 g) in isopropyl acetate (74 mL), and the mixture was stirred at room temperature for 3 hours under the hydrogen atmosphere at 1 atmospheric pressure. The reaction solution was filtrated, and washing with isopropyl acetate (15 mL) was performed. The solvent in the filtrate was distilled off, isopropyl acetate (22 mL) was added to the obtained residue, and the mixture was heated to 35° C. for dissolution. Heptane (74 mL) was added to precipitate crystals and the mixture was cooled to room temperature and the crystals were aged for 30 minutes. The obtained crystals were collected by filtration and washed with heptane (29 mL) at 0° C. The solvent in the filtrate was distilled off, and the obtained residue was purified by silica gel column chromatography (heptane:ethyl acetate=3:1), and was combined with the above crystals. MTBE (47.6 g) was added to the obtained compound at 35° C. for dissolution. Heptane (95.2 mL) and seed crystals were added to precipitate crystals. The crystals were cooled to 0° C. and aged for 30 minutes. The obtained crystals were collected by filtration and washed with heptane (23.8 mL) at 0° C. By drying under reduced pressure at 40° C., the title compound (9.72 g) having the following physical properties was obtained.

TLC: Rf 0.29 (hexane:ethyl acetate=2:1);

$^1$H-NMR (CDCl$_3$): δ 8.09, 7.67-7.60, 7.46, 7.39, 5.14, 4.99, 4.07-4.01, 3.68, 3.57, 2.97, 2.60, 2.55, 2.24, 2.08-1.81, 1.73-1.51, 1.22, 1.19-1.01.

Example 10: (3S,5aR,6R,7R,8aS)-6-formyl-3-[4-oxo-4-(2-propanyloxy)butyl]octahydro-2H-cyclopenta[b]oxepin-7-yl 4-biphenylcarboxylate

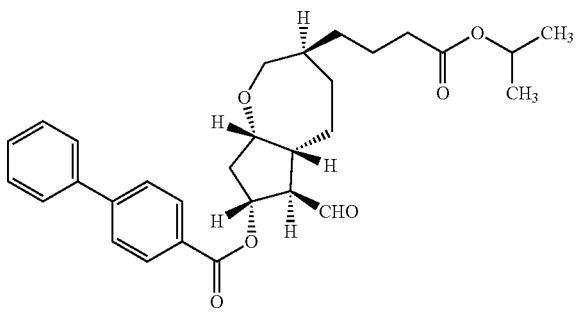 [SMILES: CC(C)OC(=O)CCC[C@H]1CC[C@@H]2[C@@H](C=O)[C@H](OC(=O)c3ccc(-c4ccccc4)cc3)C[C@@H]2OC1]

1-(3-dimethylaminopropyl)-3-ethylcarbodiimide hydrochloride (57.6 g), isopropyl acetate (240 mL) and dimethyl sulfoxide (250 mL) were added to the compound produced in Example 9 (49.5 g) and the mixture was cooled to 10° C. Dichloroacetic acid (12.9 g) was added to the mixture at 10° C. or lower, and the mixture was stirred at 10° C. for 2 hours. 1 M Hydrochloric acid (250 mL) was placed in a separate reaction vessel and the above reaction mixture was added thereto at 30° C. or lower. The liquid mixture was separated, and the organic layer was washed sequentially with 5% sodium bicarbonate aqueous solution (250 mL) and 20% brine (250 mL). The organic layer was dried over magnesium sulfate, and thereafter, was filtrated. The solvent in the filtrate was distilled off, isopropanol (250 mL) was added to the residue, and the mixture was heated to 50° C. for dissolution. The mixture was cooled to 0° C. to precipitate crystals, and water (250 mL) was added thereto. The crystals were aged at room temperature for 30 minutes, and the obtained crystals were collected by filtration. The crystals were washed with a mixed solution of isopropanol (75 mL) and water (75 mL), and dried under reduced pressure at room temperature to give the title compound (46.3 g) having the following physical properties.

TLC: Rf 0.59 (hexane:acetone=3:2);

$^1$H-NMR (CDCl$_3$): δ 9.75, 8.08, 7.67-7.61, 7.47, 7.39, 5.35, 5.00, 4.13-4.04, 2.99, 2.81, 2.71, 2.38, 2.25, 2.02, 1.97-1.89, 1.81, 1.74-1.53, 1.23, 1.19-1.04.

Example 11: (3S,5aR,6R,7R,8aS)-6-[(1E)-4-(2,5-difluorophenoxy)-3-oxo-1-buten-1-yl]-3-[4-oxo-4-(2-propanyloxy)butyl]octahydro-2H-cyclopenta[b]oxepin-7-yl 4-biphenylcarboxylate

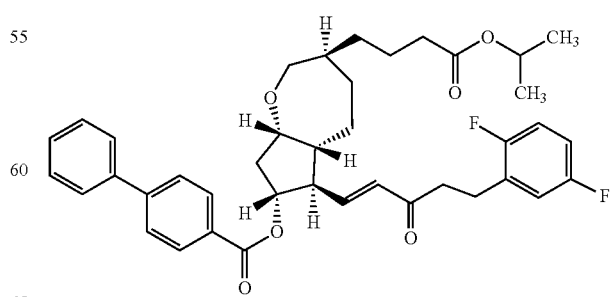

THF (400 mL), isopropanol (80 mL) and water (20 mL) were mixed to prepare Solution A. Solution A (300 mL) was added to dimethyl [3-(2,5-difluorophenoxy)-2-oxopropyl]phosphonate (41.4 g) (CAS Registry Number: 1402924-07-5), and lithium chloride (5.97 g) and triethylamine (14.2 g) were added thereto at 5° C. or lower. A solution (100 mL) of the compound produced in Example 10 (46.3 g) in Solution A was added thereto at 10° C. or lower, and the mixture was washed with Solution A (50 mL). The mixture was stirred at room temperature for 2 hours. Isopropyl acetate (200 mL) and 1 M hydrochloric acid (100 mL) were placed in a separate reaction vessel, the above reaction mixture was added thereto at 30° C. or lower and the mixture was washed with isopropyl acetate (50 mL). The liquid mixture was separated, and the organic layer was washed sequentially with 5% sodium bicarbonate aqueous solution (100 mL) and 20% brine (100 mL). The organic layer was dried over magnesium sulfate and was filtrated. The solvent in the filtrate was distilled off, and the obtained residue was purified by silica gel column chromatography (heptane:isopropyl acetate=85:15→75:25). Isopropanol (855 mL) was added to the obtained compound, and the mixture was heated to 60° C. for dissolution. The mixture was cooled to 30° C. or lower to precipitate crystals and the crystals were aged for 2 hours. The obtained crystals were collected by filtration and washed with isopropanol (170 mL). By drying under reduced pressure at room temperature, the title compound (43.0 g) having the following physical properties was obtained.

TLC: Rf 0.55 (hexane:acetone=3:2);
$^1$H-NMR (CDCl$_3$): δ 8.04, 7.62, 7.47, 7.40, 7.01-6.92, 6.59-6.55, 6.44, 5.09, 5.01, 4.74, 4.11-4.06, 2.97, 2.84, 2.71, 2.25, 2.00-1.47, 1.23, 1.20-1.01.

Example 12: (3S,5aR,6R,7R,8aS)-6-[(1E,3R)-4-(2,5-difluorophenoxy)-3-hydroxy-1-buten-1-yl]-3-[4-oxo-4-(2-propanyloxy)butyl]octahydro-2H-cyclopenta[b]oxepin-7-yl 4-biphenylcarboxylate

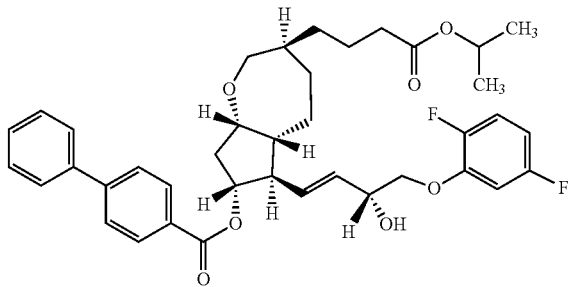 [SMILES: CC(C)OC(=O)CCC[C@H]1CC[C@@H]2[C@@H](/C=C/[C@@H](O)COc3cc(F)ccc3F)[C@H](OC(=O)c3ccc(-c4ccccc4)cc3)C[C@@H]2OC1]

Toluene (269 mL) was added to chlorobis(2,6,6-trimethylbicyclo[3.1.1]heptan-3-yl)borane (57.6% heptane solution, 89.5 g) (CAS Registry Number: 85116-37-6), the mixture was cooled to −50° C., a solution of the compound produced in Example 11 (42.0 g) in toluene (126 mL) was added thereto at −50° C. and the mixture was washed with toluene (42 mL). The mixture was stirred at −50° C. for 5.5 hours, and isopropanol (42 mL) and a solution of 2,6-di-tert-butyl-p-cresol (1.40 g) in toluene (8.4 mL) were added sequentially thereto. After raising the temperature to 0° C., a solution of phosphoric acid (22.0 g) in water (168 mL) was added to the mixture at 20° C. or lower. Toluene (84 mL) was added to the mixture, the liquid mixture was separated, and the organic layer was washed sequentially with 5% sodium bicarbonate aqueous solution (210 mL) and 20% brine (210 mL). The organic layer was dried over magnesium sulfate, and thereafter, was filtrated. The solvent in the filtrate was distilled off, and the obtained residue was purified by silica gel column chromatography (heptane:isopropyl acetate=6:1→2:1) to give the title compound (40.0 g) having the following physical properties.

TLC: Rf 0.31 (hexane:ethyl acetate=3:1);
$^1$H-NMR (CDCl$_3$): δ 8.07, 7.65-7.60, 7.49-7.45, 7.39, 6.97, 6.64-6.53, 5.78, 5.63, 5.08-4.97, 4.51, 4.10-4.03, 3.90, 3.83, 2.97, 2.77, 2.54, 2.37, 2.25, 2.02, 1.96-1.45, 1.23, 1.09-1.01.

Example 13: 2-propanyl 4-{(3S,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}butanoate

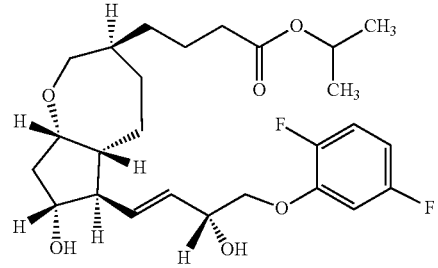 [SMILES: CC(C)OC(=O)CCC[C@H]1CC[C@@H]2[C@@H](/C=C/[C@@H](O)COc3cc(F)ccc3F)[C@H](O)C[C@@H]2OC1]

To a suspension of lithium isopropoxide (7.97 g) in isopropanol (240 mL), a solution of the compound produced in Example 12 (40.0 g) in THF (120 mL) was added at room temperature and the mixture was washed with THF (12 mL). After stirring at 45° C. for 3.5 hours, the mixture was cooled to room temperature. 1 M Hydrochloric acid (216 mL) and isopropyl acetate (360 mL) were added to the mixture at 30° C. or lower, the liquid mixture was separated, and the organic layer was washed sequentially with 5% sodium bicarbonate aqueous solution (120 mL) and 20% brine (120 mL). The organic layer was dried over magnesium sulfate, and thereafter, was filtrated. The solvent in the filtrate was distilled off, and the obtained residue was purified by silica gel column chromatography (heptane:isopropyl acetate=40:60→34:66→0:100). The obtained compound was dissolved in isopropyl acetate (46.3 mL) and the mixture was filtrated. Washing twice with isopropyl acetate (4.9 mL) was performed. The filtrate was heated to 60° C., and heptane (236 mL) was added thereto. The mixture was cooled to 40° C., and seed crystals were added to precipitate crystals. Heptane (59 mL) was further added and the mixture was cooled to room temperature and the crystals were aged for 1 hour. The obtained crystals were collected by filtration and washed with a mixed solution of isopropyl acetate (19.7 mL) and heptane (98.5 mL). By drying under reduced pressure at 45° C., the title compound (16.2 g) having the following physical properties was obtained.

TLC: Rf 0.54 (ethyl acetate);
$^1$H-NMR (CDCl$_3$): δ 0.92-1.18, 1.21, 1.34-1.82, 1.82-1.96, 2.03-2.18, 2.23, 2.28, 2.41-2.54, 2.78, 2.84-2.98, 3.62-3.80, 3.86-4.11, 4.47-4.61, 4.89-5.07, 5.54-5.76, 6.54-6.66, 6.66-6.76, 6.93-7.05.

According to the above Examples, for example, when the starting material (3 aR,4S,5R,6aS)-4-[(benzyloxy)methyl]-2-oxohexahydro-2H-cyclopenta[b]furan-5-yl 4-phenylbenzoate was 70 g, the total yield of the present compound was about 18%. On the other hand, according to the known production method, for example, when the starting material (3aR,4S,5R,6aS)-4-(hydroxymethyl)-5-(tetrahydro-2H-pyran-2-yloxy)hexahydro-2H-cyclopenta[b]furan-2-one was 20 g, the total yield of the present compound was about 0.058%. Further, the yield of the desired diastereomer in Example 8 of the present invention (specifically, in the compound described in Example 8, the compound of which the asymmetric carbon atom at the 3-position (carbon atom to which the α chain in the so-called prostaglandin skeleton is bonded) is in the S configuration) was about 90%, whereas in the corresponding Example 9→Example 10 of the known production method, the yield of the desired diastereomer was about 60%. Accordingly, it was revealed that the total yield of the production method according to the present invention is higher than that of the known production method, and the production method according to the present invention can stably supply the present compound.

INDUSTRIAL APPLICABILITY

According to the present invention, since the total reaction yield is high and the present compound can be stably supplied, the present invention can be a useful method for producing the present compound which can be used on an industrial production scale.

The invention claimed is:
1. A method for producing a compound represented by formula (G) or a salt thereof:

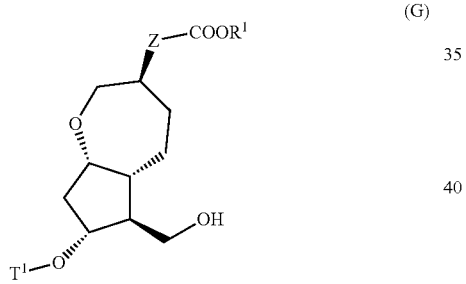

wherein, $R^1$ represents a C1-6 alkyl group optionally substituted with a hydroxyl group or a C1-4 alkoxy group, Z represents (1) —$(CH_2)_m$—, (2) —$(CH_2)_n$—CH=CH—, or (3) —$(CH_2)_p$-A-$CH_2$—, A represents an oxygen atom, or a sulfur atom, m represents an integer of 1 to 6, n represents an integer of 1 to 4, and p represents an integer of 1 to 4, and $T^1$ represents (1) a p-phenybenzoyl group, (2) a methyl group, (3) a trityl group, (4) a methoxymethyl group, (5) a 1-ethoxyethyl group, (6) a methoxyethoxymethyl group, (7) a benzyloxymethyl group, (8) a trimethylsilyl group, (9) a triethylsilyl group, (10) a t-butyldimethylsilyl group, (11) a t-butyldiphenylsilyl group, (12) a triisopropylsilyl group, (13) a benzyl group, (14) a p-methoxybenzyl group, (15) an acetyl group, (16) a pivaloyl group, (17) a benzoyl group, (18) an allyloxycarbonyl group, (19) a 2,2,2-trichloroethoxycarbonyl group, (20) a t-butoxycarbonyl group, (21) an allyl group, or (22) a tosyl group,
the method comprising the following steps (i) to (vi):
step (i): subjecting a compound represented by formula (A):

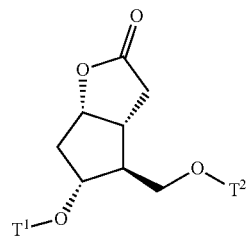

wherein, $T^2$ represents a benzyl group, and other symbols represent the same meanings as those described above, to a reduction reaction to produce a compound represented by formula (B):

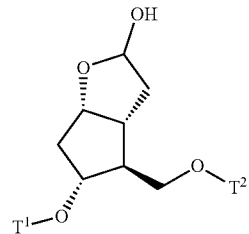

wherein, all symbols represent the same meanings as those described above,
or a salt thereof;
step (ii): subjecting the compound represented by formula (B) obtained in the step (i) or a salt thereof to a reaction in an organic solvent, in the presence of a base using a Wittig reagent to produce a compound represented by formula (C):

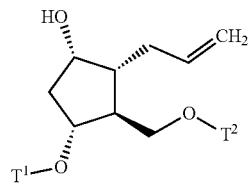

wherein, all symbols represent the same meanings as those described above,
or a salt thereof;
step (iii): subjecting the compound represented by the formula (C) obtained in the step (ii) or a salt thereof and a compound represented by formula (a):

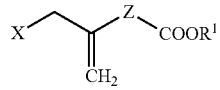

wherein, X represents a halogen atom, a tosyloxy (TsO) group, or a mesyloxy (MsO) group, and other symbols represent the same meanings as those described above,
to an alkylation reaction to produce a compound represented by formula (D):

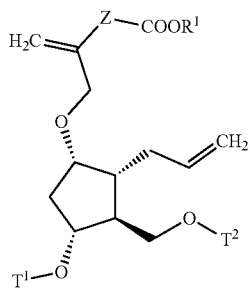

(D)

wherein, all symbols represent the same meanings as those described above;

step (iv): subjecting the compound represented by the formula (D) obtained in the step (iii) to a metathesis reaction to produce a compound represented by formula (E):

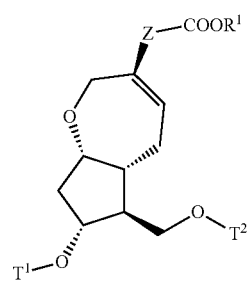

(E)

wherein, all symbols represent the same meanings as those described above;

step (v): subjecting the compound represented by the formula (E) obtained in the step (iv) to an asymmetric reduction reaction to produce a compound represented by formula (F):

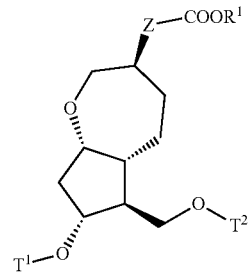

(F)

wherein, all symbols represent the same meanings as those described above; and step (vi): subjecting the compound represented by the formula (F) obtained in the step (v) to a deprotection reaction to produce the compound represented by the formula (G) or a salt thereof.

2. A method for producing a compound represented by formula (K):

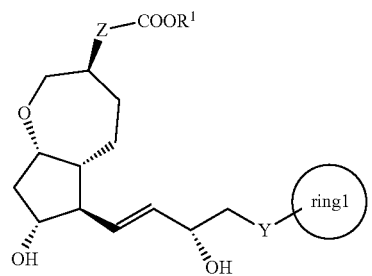

(K)

wherein, Y represents —$CH_2$—, —O— or —S—,

 represents a C3-10 carbocycle or a 3- to 10-membered heterocycle optionally substituted with 1 to 5 substituents selected from the group consisting of (1) a halogen atom, (2) $CF_3$, (3) $OCF_3$, (4) a C1-4 alkoxy group, (5) a C1-4 alkyl group, (6) a hydroxyl group, and (7) a nitrile group, $R^1$ represents a C1-6 alkyl group optionally substituted with a hydroxyl group or a C1-4 alkoxy group, Z represents (1) —$(CH_2)_m$—, (2) —$(CH_2)_n$—CH=CH—, or (3) —$(CH_2)_p$-A-$CH_2$—, A represents an oxygen atom, or a sulfur atom, m represents an integer of 1 to 6, n represents an integer of 1 to 4, and p represents an integer of 1 to 4, the method comprising:

producing a compound represented by formula (G) or a salt thereof from a compound represented by formula (A) according to steps (i) to (vi):

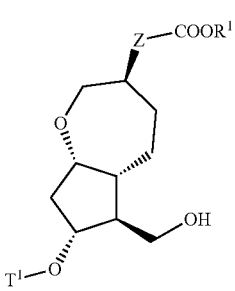

(G)

wherein, $T^1$ represents (1) a p-phenybenzoyl group, (2) a methyl group, (3) a trityl group, (4) a methoxymethyl group, (5) a 1-ethoxyethyl group, (6) a methoxyethoxymethyl group, (7) a benzyloxymethyl group, (8) a trimethylsilyl group, (9) a triethylsilyl group, (10) a t-butyldimethylsilyl group, (11) a t-butyldiphenylsilyl group, (12) a triisopropylsilyl group, (13) a benzyl group, (14) a p-methoxybenzyl group, (15) an acetyl group, (16) a pivaloyl group, (17) a benzoyl group, (18) an allyloxycarbonyl group, (19) a 2,2,2-trichloroethoxycarbonyl group, (20) a t-butoxycarbonyl group, (21) an allyl group, or (22) a tosyl group, and other symbols represent the same meanings as those described above, step (i): subjecting a compound represented by formula (A):

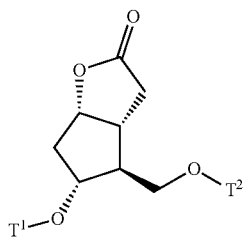
(A)

wherein, T² represents a benzyl group, and other symbols represent the same meanings as those described above, to a reduction reaction to produce a compound represented by formula (B):

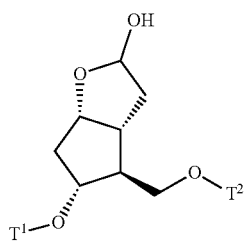
(B)

wherein, all symbols represent the same meanings as those described above,
or a salt thereof;

step (ii): subjecting the compound represented by formula (B) obtained in the step (i) or a salt thereof to a reaction in an organic solvent, in the presence of a base using a Wittig reagent to produce a compound represented by formula (C):

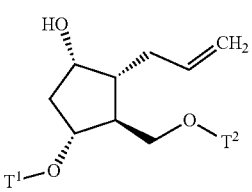
(C)

wherein, all symbols represent the same meanings as those described above,
or a salt thereof;

step (iii): subjecting the compound represented by the formula (C) obtained in the step (ii) or a salt thereof and a compound represented by formula (a):

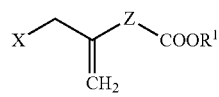
(a)

wherein, X represents a halogen atom, a tosyloxy (TsO) group, or a mesyloxy (MsO) group, and other symbols represent the same meanings as those described above, to an alkylation reaction to produce a compound represented by formula (D):

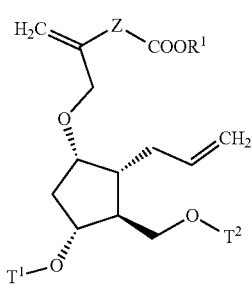
(D)

wherein, all symbols represent the same meanings as those described above;

step (iv): subjecting the compound represented by the formula (D) obtained in the step (iii) to a metathesis reaction to produce a compound represented by formula (E):

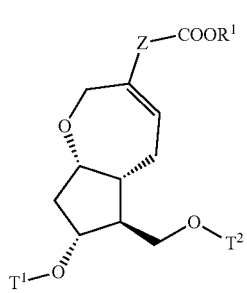
(E)

wherein, all symbols represent the same meanings as those described above;

step (v): subjecting the compound represented by the formula (E) obtained in the step (iv) to an asymmetric reduction reaction to produce a compound represented by formula (F):

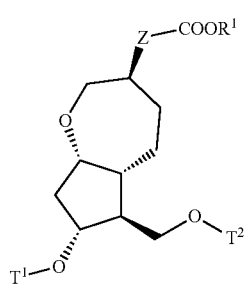
(F)

wherein, all symbols represent the same meanings as those described above; and step (vi): subjecting the compound represented by the formula (F) obtained in the step (v) to a deprotection reaction to produce the compound represented by the formula (G) or a salt thereof;

producing a compound represented by formula (I) or a salt thereof from the compound represented by the formula (G) or a salt thereof according to steps (vii) to (viii):

(I)

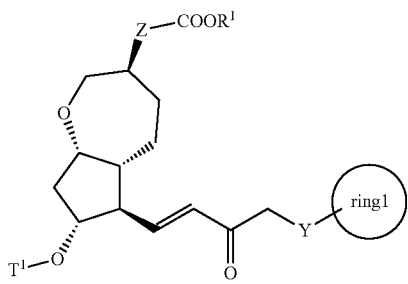

wherein, all symbols represent the same meanings as those described above, step (vii): subjecting a compound represented by formula (G):

(G)

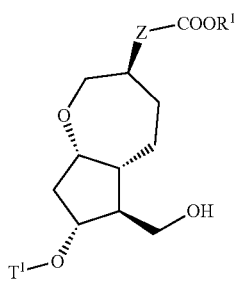

wherein, all symbols represent the same meanings as those described above, or a salt thereof to an oxidation reaction to produce a compound represented by formula (H):

(H)

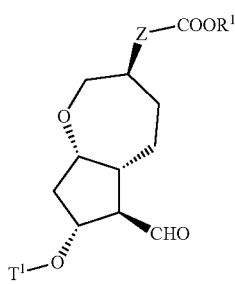

wherein, all symbols represent the same meanings as those described above; and step (viii): subjecting the compound represented by the formula (H) obtained in the step (vii) and a compound represented by formula (b):

(b)

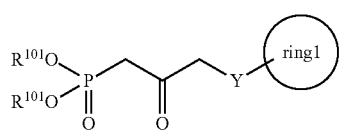

wherein, $R^{101}$ represents a C1-6 alkyl group, and other symbols represent the same meanings as those described above, to a reaction in an organic solvent, in water, or in a mixed solution thereof, in the presence of a base, in the presence or absence of an additive to produce the compound represented by the formula (I) or a salt thereof; and producing the compound represented by the formula (K) according to steps (ix) to (x):

step (ix): subjecting a compound represented by formula (I):

(I)

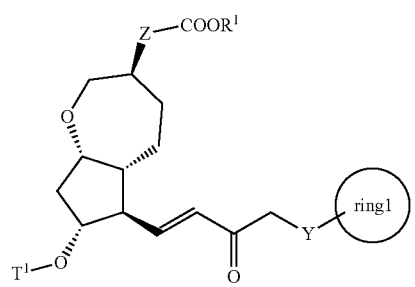

wherein, all symbols represent the same meanings as those described above, or a salt thereof, to an asymmetric reduction reaction to produce a compound represented by formula (J) or a salt thereof:

(J)

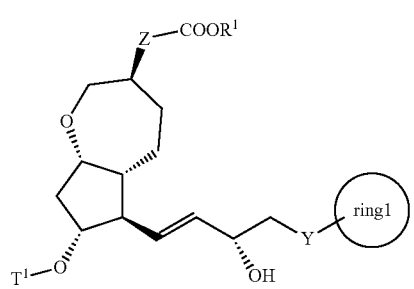

wherein all symbols represent the same meanings as those described above; and step (x): subjecting the compound represented by the formula (J) or a salt thereof to a deprotection reaction to produce the compound represented by the formula (K).

3. The method according to claim 1, wherein $T^1$ is a p-phenybenzoyl group.

4. The method according to claim 2, wherein the compound represented by the formula (K) is 2-propanyl 4-{(3S,5aR,6R,7R,8aS)-6-[(1E,3R)-4-(2,5-difluorophenoxy)-3-hydroxy-1-buten-1-yl]-7-hydroxyoctahydro-2H-cyclopenta[b]oxepin-3-yl}butanoate.

5. The method according to claim 2, wherein $T^1$ is a p-phenybenzoyl group.

* * * * *

UNITED STATES PATENT AND TRADEMARK OFFICE
CERTIFICATE OF CORRECTION

PATENT NO. : 10,899,729 B2  
APPLICATION NO. : 16/314555  
DATED : January 26, 2021  
INVENTOR(S) : Hideki Moriguchi et al.

Page 1 of 1

It is certified that error appears in the above-identified patent and that said Letters Patent is hereby corrected as shown below:

On the Title Page

Column 1, item (73) Assignee, delete "CO.." and insert --CO.,-- therefor;

In the Claims

In Claim 2, Column 33, Line 63, delete "(Ts0)" and insert --(TsO)-- therefor;

In Claim 2, Column 33, Line 64, delete "(Ms0)" and insert --(MsO)-- therefor.

Signed and Sealed this  
Fifteenth Day of June, 2021

Drew Hirshfeld  
*Performing the Functions and Duties of the*  
*Under Secretary of Commerce for Intellectual Property and*  
*Director of the United States Patent and Trademark Office*